(12) United States Patent
Morgan et al.

(10) Patent No.: US 10,881,701 B2
(45) Date of Patent: *Jan. 5, 2021

(54) METHOD FOR PROVIDING SUPPORT DURING VACCINATIONS AND DURING ADAPTIVE IMMUNE SYSTEM RESPONSE

(71) Applicants: Sarah Morgan, Aurora, CO (US); Karl Holtzer, Pittsburgh, PA (US)

(72) Inventors: Sarah Morgan, Aurora, CO (US); Karl Holtzer, Pittsburgh, PA (US)

( * ) Notice: Subject to any disclaimer, the term of this patent is extended or adjusted under 35 U.S.C. 154(b) by 128 days.

This patent is subject to a terminal disclaimer.

(21) Appl. No.: 16/427,605

(22) Filed: May 31, 2019

(65) Prior Publication Data

US 2020/0261525 A1   Aug. 20, 2020

Related U.S. Application Data

(62) Division of application No. 16/280,356, filed on Feb. 20, 2019.

(51) Int. Cl.
| | | |
|---|---|---|
| *A01N 43/00* | (2006.01) |
| *A01N 43/46* | (2006.01) |
| *A61K 31/55* | (2006.01) |
| *A61K 36/28* | (2006.01) |
| *A61K 31/355* | (2006.01) |
| *A61K 31/375* | (2006.01) |
| *A61K 31/122* | (2006.01) |
| *A61K 31/07* | (2006.01) |
| *A61K 31/593* | (2006.01) |
| *A61K 31/714* | (2006.01) |
| *A61K 31/4415* | (2006.01) |
| *A61K 31/51* | (2006.01) |
| *A61K 31/525* | (2006.01) |
| *A61K 31/455* | (2006.01) |
| *A61K 31/197* | (2006.01) |
| *A61K 31/519* | (2006.01) |
| *A61K 31/19* | (2006.01) |
| *A61K 33/18* | (2006.01) |
| *A61K 31/194* | (2006.01) |
| *A61K 31/555* | (2006.01) |
| *A61K 31/14* | (2006.01) |
| *A61K 33/06* | (2006.01) |
| *A61K 39/00* | (2006.01) |

(52) U.S. Cl.
CPC .............. *A61K 36/28* (2013.01); *A61K 31/07* (2013.01); *A61K 31/122* (2013.01); *A61K 31/14* (2013.01); *A61K 31/19* (2013.01); *A61K 31/194* (2013.01); *A61K 31/197* (2013.01); *A61K 31/355* (2013.01); *A61K 31/375* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/555* (2013.01); *A61K 31/593* (2013.01); *A61K 31/714* (2013.01); *A61K 33/06* (2013.01); *A61K 33/18* (2013.01); *A61K 39/00* (2013.01)

(58) Field of Classification Search
None
See application file for complete search history.

(56) References Cited

U.S. PATENT DOCUMENTS

| 2006/0280840 A1* | 12/2006 | Robertson | ............. A23L 33/185 426/72 |
| 2014/0017337 A1* | 1/2014 | Amoruso | ............. A61K 31/198 424/643 |

* cited by examiner

*Primary Examiner* — Layla Soroush
(74) *Attorney, Agent, or Firm* — Kearney, McWilliams & Davis, PLLC; William C. Yarbrough

(57) ABSTRACT

The present invention provides formulations and methods for formulation administration that support an individual's body during vaccination and adaptive immune response. The individuals who can benefit from these formulations and methods for formulation administration are infants, children and adults. The formulations comprise ingredients that may be administered prior to, concurrent with or subsequent to the vaccination. The formulations and methods for formulation administration of the present invention preferably act by selectively targeting enzymatic reactions, epigenetic expression, and an individual's various metabolic pathways in support of immune system homeostasis, maintaining balance between oxidative stress and methylation, fostering balance between Th1 and Th2 responses, or a combination thereof, during vaccination and adaptive immune responses to improve vaccine response and reduce vaccine side effects.

4 Claims, No Drawings

METHOD FOR PROVIDING SUPPORT DURING VACCINATIONS AND DURING ADAPTIVE IMMUNE SYSTEM RESPONSE

CROSS-REFERENCE TO RELATED APPLICATION

This nonprovisional application claims benefit of provisional application U.S. Ser. No. 62/200,446 filed Aug. 3, 2015, provisional application U.S. Ser. No. 62/345,227 filed Jun. 30, 2016, nonprovisional application Ser. No. 15/226,415 filed Aug. 2, 2016, and nonprovisional application U.S. Ser. No. 16/280,356 filed Feb. 20, 2019.

FEDERAL FUNDING LEGEND

This invention was not created using federal funds.

BACKGROUND OF THE INVENTION

Field of the Invention

The present invention generally relates to formulations that provide support to an individual's body during vaccinations and adaptive immune and methods thereof. More specifically, the present invention is drawn to formulations that comprise novel combinations of ingredients that target epigenetic regulation of gene expression, specific enzymatic reactions, cytokine differentiation and immune system homeostasis in various metabolic pathways in an individual during vaccination and adaptive immune system response. The administration of the formulation may improve antibody response and decrease vaccine side effects to provide and safer and more effective vaccinations for the population at large by improving the synthesis and release of cellular biomarkers.

Background

The mitochondrion is known to function as the powerhouse of the cell because it produces the energy that an individual's body requires to survive. However, in this process of energy production, it produces reactive oxygen species that are harmful to the body. Glutathione is a primary antioxidant that protects the body from the harmful effects of reactive oxygen species such as free radicals, heavy metals and peroxides. Glutathione is a tripeptide made up of three amino acids (glutamate, glycine and cysteine). Cysteine, which is the rate limiting factor in glutathione synthesis can either be made in the cell by a process called transsulfuration or can be obtained from outside the cell, for instance, from diet or through nutrient support.

Glutathione exists in two forms, including reduced glutathione (GSH) and the non-reactive, oxidized form (glutathione disulfide form; GSSG) depending on the amount of electrons it carries. Glutathione is in a reactive state when it is reduced (GSH) and in a non-reactive state when it is oxidized (GSSG). Reduced glutathione (GSH) gives up an electron, and thus becomes reactive, but then readily bonds with another oxidative glutathione molecule to form non-reactive glutathione disulfide (GSSG). GSSG is a disulfide formed from the bonding of two oxidative glutathione molecules. The bonding neutralizes the two oxidative glutathione molecules. Due to the rapid nature of the reduction of the oxidized form of glutathione relative to its synthesis or secretion, the ratio of reduced glutathione to oxidized glutathione is a good indicator of the oxidative stress within cells.

Oxidative stress is important for reasons including but not limited to its ability to inhibit methylation. However, methylation is very essential as it is involved in the single carbon transfer of molecules. Defects in single carbon transfer are associated with many different diseases and cellular dysfunction. One of the most essential methylation reactions involves DNA, histone and specific CpG island methylation, which has implications with regard to gene expression, cytokine differentiation and immune regulation. Methylation is also involved in certain enzymatic pathways and bodily functions that include but are not limited to creatine and adenosine synthesis (energy production), phospholipid synthesis (cellular membrane integrity), serotonin and melatonin production, biopterin (BH4) synthesis (amino acid metabolism), glutathione synthesis, arginine metabolism (nitrous oxide synthesis), catecholamine production (cognitive status), and CpG island methylation for adequate production of interferon gamma for immune system homeostasis. Thus, disruption of methylation equilibrium plays a critical role in global disease states and may play a role in vaccine response.

Conventional methods and formulations lack the ability to beneficially target gene expression for proper enzymatic reactions involved in metabolic pathways, in vaccine response and in adaptive immune response including but not limited to those involved in maintaining the delicate balance between methylation, transsulfuration, and oxidative stress for healthy cellular metabolism. Further, there is a current lack of focus on the mechanisms that cause individuals to respond or not respond to standard vaccine protocols. Thus, there is a long-felt but significant and un-met need in the art for formulations and methods that can beneficially target such enzymatic reactions, and help essentially maintain the delicate balance between methylation, transsulfuration, and oxidative stress—or a combination thereof to improve vaccine response and reduce vaccine side effects. Still further, there is a long-felt and significant but un-met need in the art of supportive immunization protocols that can target epigenetic expression, enzymatic kinetics and immune system homeostasis to improve vaccine response and reduce side effects. The present invention satisfies this long standing need in the art.

SUMMARY OF EMBODIMENTS OF THE INVENTION

In a preferred embodiment, the present invention is directed to a formulation, comprising: thiamine (Vitamin B1), a derivative thereof or an analog thereof; riboflavin (Vitamin B2), a derivative thereof or an analog thereof, niacin (Vitamin B3), a derivative thereof or an analog thereof; pantothenic acid (Vitamin B5), a derivative thereof or an analog thereof; Vitamin B6, a derivative thereof or an analog thereof; folate (Vitamin B9), a derivative thereof or an analog thereof; cobalamin (Vitamin B12), a derivative thereof or an analog thereof; Vitamin A, a derivative thereof or an analog thereof; Vitamin D, a derivative thereof or an analog thereof; Vitamin E, a derivative thereof or an analog thereof, Vitamin C, a derivative thereof or an analog thereof; Vitamin K, a derivative thereof or an analog thereof; calcium, a derivative thereof or an analog thereof; iodine, a derivative thereof or an analog thereof: magnesium, a derivative thereof or an analog thereof; zinc, a derivative thereof or an analog thereof; selenium, a derivative thereof or an analog thereof; manganese, a derivative thereof or an analog thereof; chromium, a derivative thereof or an analog thereof; molybdenum, a derivative thereof or an analog thereof; trimethylglycine (betaine), a derivative thereof or an analog thereof; choline, a derivative thereof or an analog thereof; acetyl-L-carnitine, a derivative thereof or an analog thereof; N-acetyl cysteine, a derivative thereof or an analog thereof; milk thistle (*Silybum marianum*, preferably at least 80% silymarin), a derivative thereof or an analog thereof; creatinine, a derivative thereof or an analog thereof; or a combination thereof.

In another embodiment, the ingredients in the formulation are in the pure form, substantially pure form or synthetic form.

In yet another embodiment, the formulation comprises about 0.1 mg-10 mg, preferably about 0.5 mg of thiamin, about 0.1 mg-500 mg, preferably about 5 mg of riboflavin, about 0.5 mg-1 g, preferably about 5 mg of niacin, about 0.5 mg-10 mg, preferably about 2 mg of pantothenic acid, about 0.1 mg-25 mg, preferably about 2 mg of Vitamin B6, about 5 mcg-1 mg, preferably about 100 mcg of folate, about 10 mcg-5,000 mcg, preferably about 50 mcg of cobalamin, about 10 mcg-1,000 mcg, preferably about 100 mcg of Vitamin A, about 50 IU-1,000 IU, preferably about 400 IU of Vitamin D, about 1 mg-20 mg, preferably about 5 mg of Vitamin E, about 5 mg-5,000 mg, preferably about 50 mg of Vitamin C, about 0.5 mcg-300 mcg, preferably about 2.5 mcg of Vitamin K, about 50 mg-800 mg, preferably about 200 mg of calcium, about 20 mcg-15 mg, preferably about 130 mcg iodine, about 5 mg-200 mg, preferably about 75 mg of magnesium, about 1 mg-15 mg, preferably about 2.5 mg of zinc, about 5 mcg-200 mcg, preferably about 25 mcg of selenium, about 0.1 mg-5 mg, preferably about 0.6 mg of manganese, about 1 mcg-150 mcg, preferably about 10 mcg of chromium, about 1 mcg-100 mcg, preferably about 20 mcg of molybdenum, about 100 mg-5 g, preferably about 500 mg of trimethylglycine (betaine), about 10 mg-1 g, preferably about 20 mg of choline, about 50 mg-2 g, preferably about 200 mg of acetyl-L-carnitine, about 20 mg-500 mg, preferably about 100 mg of N-acetyl cysteine, about 50 mg-800 mg, preferably about 200 mg of milk thistle (*Silybum marianum*, 80% silymarin), about 20 mg-800 mg, preferably about 100 mg of creatinine or a combination thereof.

In still yet another embodiment, the formulation further comprises a pharmaceutically acceptable carrier, an excipient or a combination thereof.

In further yet another embodiment, the excipient includes but is not limited to a flavoring agent, a coloring agent, a stabilizing agent, a binder, or a disintegrant.

In yet another embodiment, the formulation has beneficial effects on immune system, detoxification, cell membrane integrity, s-adenosylmethionine (SAM) production, DNA synthesis and repair, glutathione production, nervous system or a combination thereof.

In still yet another embodiment, the formulation maintains balance or substantially maintains balance between oxidative stress and methylation, maintains balance between Th1 and Th2 response, targets specific enzymatic reactions in metabolic pathways, targets epigenetic regulation of gene expression, targets cytokine differentiation, or a combination thereof.

In further yet another embodiment, the formulation targets enzymatic reactions in metabolic pathways comprising trans-methylation, trans-sulfuration, citric acid cycle, biopterin production, amino acid metabolism, mitochondrial function, or a combination thereof.

In still further yet another embodiment, the formulation maintains the balance between the Th1 and Th2 responses by regulating methylation of specific CpG islands, production of cytokines responsible for maintaining balance between Th1 and Th2 response, or both.

In yet another embodiment, the cytokine production is regulation by regulating production of IFN-γ, IL-4, IL-5, IL-13, IL-10, IL-25, IL-31, or IL-33.

In another preferred embodiment, the present invention is directed to a method of supporting an individual's body during vaccination, during adaptive immune response or both, comprising: administering pharmacologically acceptable amount of the formulation described herein to the individual.

In yet another embodiment, the formulation is administered prior to the administration of the vaccine, concurrent with the administration of the vaccine or subsequent to the administration of the vaccine.

In still yet another embodiment, the formulation is administered orally, intramuscularly, intradermally, intravenously, nasally, subcutaneously, or intraperitoneally.

In further yet another embodiment, the administered formulation maintains balance or substantially maintains balance between oxidative stress and methylation, maintains balance between Th1 and Th2 response, targets specific enzymatic reactions in metabolic pathways, targets epigenetic regulation of gene expression, targets cytokine differentiation, or a combination thereof.

In still further yet another embodiment, the administered formulation targets enzymatic reactions in metabolic pathways comprising trans-methylation, trans-sulfuration, citric acid cycle, biopterin production, amino acid metabolism, mitochondrial function, or a combination thereof.

In another embodiment, the administered formulation maintains the balance between the Th1 and Th2 responses by regulating methylation of specific CpG islands, production of cytokines responsible for maintaining balance between Th1 and Th2 response, or both.

In yet another embodiment, the cytokine production is regulated by regulating production of IFN-γ, IL-4, IL-5, IL-13, IL-10, IL-25, IL-31, or IL-33.

In still yet another embodiment, the individual is an infant, a toddler, a teenager, or an adult.

DETAILED DESCRIPTION

The present invention discloses preferred formulations that beneficially target certain enzymatic reactions in metabolic pathways, essentially maintain the balance between oxidative stress and methylation or both. The formulation described herein provides support to the bodies of infants, children and adults during vaccination. Additionally, the formulation also provides support to the individual's body during adaptive immune response. It is contemplated herein that the formulation will target epigenetic regulation of gene expression, specific enzymatic reactions, cytokine differentiation or a combination thereof in the individual's body. It is also contemplated herein that the formulation will play a role in maintaining proper balance between T helper 1 cell (Th1) and T helper 2 cell (Th2) responses. It is further contemplated the formulation maintains Th1 and Th2 responses by regulating mechanisms including but not limited to the methylation of specific CpG islands, production of cytokines responsible for maintaining the balance between Th1 and Th2 response, or both. Examples of the cytokines responsible for maintaining the balance of Th1 and Th2 response include but are not limited to interferon gamma (IFN-γ), IL-4, IL-5, IL-13, IL-10 IL-25, IL-31, or IL-33. The metabolic pathways affected by the formulations of the present invention include, but are not limited to, trans-methylation, trans-sulfuration, citric acid cycle, biopterin production, amino acid metabolism and mitochondrial function. The formulations of the present invention have further beneficial effects on various metabolic and biochemical reactions and systems including but not limited to the immune system, detoxification, cell membrane integrity, s-adenosylmethionine (SAM) production, DNA synthesis and repair, glutathione production and beneficial effects on the nervous system.

Table 1 provides the ingredients in a representative, preferred formulation with the representative forms and representative dosages per serving.

TABLE 1

| Ingredient | Representative Form | Representative Dosage per serving (range) | Representative Preferred Dosage per serving |
|---|---|---|---|
| Thiamin (B1) | Thiamine hydrochloride | 0.1 mg-10 mg | 0.5 mg |
| Riboflavin (B2) | Riboflavin and riboflavin-5-phosphate sodium | 0.1 mg-500 mg | 5 mg |
| Niacin (B3) | Niacinamide | 0.5 mg-1 g | 5 mg |
| Pantothenic acid (B5) | D-calcium pantothenate | 0.5 mg-10 mg | 2 mg |
| B6 | Pyridoxal-5-phosphate and pyridoxine HCl | 0.1-25 mg | 2 mg |
| Folate (B9) | L-5-MTHF (L-5-methyltetrahydrofolate) | 5 mcg-1 mg | 100 mcg |
| Cobalamin (B12) | Methylcobalamin and adenosylcobalamin | 10 mcg-5,000 mcg | 50 mcg |
| Vitamin A | Beta carotene and retinyl palmitate | 10 mcg-1,000 mcg | 100 mcg |
| Vitamin D | D3 cholecalciferol | 50 IU-1,000 IU | 400 IU |
| Vitamin E | d-alpha tocopheryl succinate and mixed tocopherols | 1 mg-20 mg | 5 mg |
| Vitamin C | Ascorbic acid | 5 mg-5,000 mg | 50 mg |
| Vitamin K | Menaquinone | 0.5 mcg-300 mcg | 2.5 mcg |
| Calcium | Calcium lactate | 50 mg-800 mg | 200 mg |
| Iodine | Iodine and iodide | 20 mcg-15 mg | 130 mcg |
| Magnesium | Magnesium bis/glycinate | 5 mg-200 mg | 75 mg |
| Zinc | Zinc citrate (40% elemental) | 1 mg-15 mg | 2.5 mg |
| Selenium | AA complex, chelate (L-selenomethionine) | 5 mcg-200 mcg | 25 mcg |
| Manganese | Manganese bisglycinate/chelate | 0.1 mg-5 mg | 0.6 mg |
| Chromium | Nicotinate glycinate chelate | 1 mcg-150 mcg | 10 mcg |
| Molybdenum | Glycinate/chelate | 1 mcg-100 mcg | 20 mcg |
| Trimethylglycine (betaine) | Pure or substantially pure | 100 mg-5 g | 500 mg |
| Choline | Choline bitartrate | 10 mg-1 g | 20 mg |
| L-carnitine | Acetyl-L-carnitine | 50 mg-2 g | 200 mg |
| N-acetyl cysteine | Pure or substantially pure | 20 mg-500 mg | 100 mg |
| Milk thistle (*silybum mariamari*) (80% silymarin) | Pure or substantially pure | 50 mg-800 mg | 200 mg |
| Creatine | Pure or substantially pure creatine magnesium chelate | 20 mg-800 mg | 100 mg |

While Table 1 shows one example of the ingredients in a representative, preferred formulation with the representative forms and representative dosages per serving, the present invention broadly encompasses other formulations that have variations in the types of ingredients, forms and dosages per serving. Each ingredient in the formulation plays a specific role in providing support to an individual's body during vaccination and adaptive immune response. For instance, the B vitamins are involved in energy metabolism with specific B vitamins targeted at methylation. The cysteine in the formulation may be the rate limiting amino acid in glutathione production. The choline in the formulation is an integral component to cellular membrane stability that is implicated severely by oxidative stress and methylation defects. The milk thistle (*Silybum marianum*) in the formulation may exert a hepatoprotective effect through a number of mechanisms including but not limited to antioxidant activity, toxin blockade at the membrane level, enhanced protein synthesis, anti-inflammatory effect, or immuno-modulating effect. This is important because the liver is one of the most metabolically active organs with over 2,500 mitochondria per hepatocyte and is the main location for cellular metabolism, and maintaining equilibrium between methylation, transsulfuration, and oxidative stress. The carnitine in this formulation may act as an antioxidant and support the mitochondrial function through mechanisms including but not limited to fatty acid metabolism and energy production. The trimethylglycine in this formulation may act to support whole body methylation by providing methyl donors, increasing S-adenosyl methionine levels and reducing homocysteine levels. Trimethylglycine may also act as an osmolyte to aid in cellular hydration status. The creatine in this formulation may help to support energy metabolism and lighten the majority demand of methyltransferase activity by providing the end product of guanidinoacetate N-methyltransferase (GAMT). The other ingredients in the formulation either support overall cellular physiology through energy production (enhancing mitochondrial function) or through their well-known antioxidant capabilities, thereby enhancing the delicate balance between oxidative stress and methylation.

Each ingredient that is used in a formulation of the present invention may be used in a pure form, or a substantially pure form, as determined by any suitable method for determination of purity that is well accepted and established.

It is also to be understood that the inventors have contemplated that any active isomer or metabolite of any ingredient listed in Table 1, or any combination thereof, may also be used in a formulation of the present invention.

In one embodiment, the present invention provides a formulation comprising a combination of ingredients to support the body of an individual during vaccination, adaptive immune response, or both, wherein the formulation acts by targeting specific enzymatic reactions in metabolic pathways, target epigenetic regulation of gene expression, target cytokine differentiation, maintain balance or substantially maintain balance between oxidative stress and methylation, maintain proper balance between Th 1 and Th2 responses, or a combination thereof. In another embodiment, the formulation maintains balance between Th1 and Th2 responses by regulating mechanisms including but not limited to the methylation of specific CpG islands, production of cytokines responsible for maintaining balance between Th1 and Th2 response, or both. In yet another embodiment, the cytokine production regulated by the formulation includes but is not limited to the production of IFN-γ, IL-4, IL-5, IL-13, IL-10, IL-25, IL-31, or IL-33. In further yet another embodiment, the formulations targets enzymatic reactions involved in metabolic pathways including but not limited to trans-methylation, trans-sulfuration, citric acid cycle, biopterin production, amino acid metabolism and mitochondrial function.

In another embodiment, the formulation comprises thiamin (Vitamin B1), riboflavin (Vitamin B2), niacin (Vitamin B3), pantothenic acid (Vitamin B5), Vitamin B6, folate (Vitamin B9), cobalamin (Vitamin B12), Vitamin A, Vitamin D, Vitamin E, Vitamin C, Vitamin K, calcium, iodine, magnesium, zinc, selenium, manganese, chromium, molybdenum, trimethylglycine (betaine), choline, acetyl-L-carnitine, N-acetyl cysteine, milk thistle (*Silybum marianum*, 80% silymarin), creatinine or a combination thereof.

In certain embodiments, a formulation of the present invention may include thiamine or a derivative of thiamine including but not limited to thiamine hydrochloride, an analog of thiamine or a combination thereof. The formulation may also include, for instance, thiamine mononitrate or thiamine nitrate.

In certain embodiments, a formulation of the present invention may include riboflavin or a derivative of riboflavin including but not limited to riboflavin-5-phosphate sodium, an analog of riboflavin or a combination thereof.

In certain embodiments, a formulation of the present invention may include niacin or a derivative of niacin including but not limited to niacinamide, an analog of niacin or a combination thereof. Any suitable form of niacin may be used such as, for example, nicotinic acid (pyridine-3-carboxylic acid), nicotinamide (nicotinic acid amide), and other derivatives (e.g., inositol hexanicotinate) that exhibit the biological activity of nicotinamide.

In certain embodiments, a formulation of the present invention may include pantothenic acid or a derivative of pantothenic acid including but not limited to D-calcium pantothenate, an analog of pantothenic acid or a combination thereof.

In certain embodiments, a formulation of the present invention may include a B6 or a derivative of B6 including but not limited to pyridoxal-5-phosphate, pyridoxine HCl, an analog of B6 or a combination thereof.

In certain embodiments, a formulation of the present invention may include folate or a derivative of folate including but not limited to L-5-methyltetrahydrofolate (L-5-MTHF), an analog of folate or a combination thereof. L-methylfolate calcium, metafolin, or levomefolic acid may also be used.

In certain embodiments, a formulation of the present invention may include cobalamin or a derivative of cobalamin including but not limited to methylcobalamin, adenosylcobalamin, hydroxycobalamin, an analog of cobalamin or a combination thereof.

In certain embodiments, a formulation of the present invention may include vitamin A or a derivative of vitamin A including but not limited to beta carotene and retinyl palmitate, an analog of vitamin A or a combination thereof.

In certain embodiments, a formulation of the present invention may include vitamin D or a derivative of vitamin D including but not limited to D3 cholecalciferol, an analog of vitamin D or a combination thereof.

In certain embodiments, a formulation of the present invention may include vitamin E or a derivative of vitamin E including but not limited to d-alpha tocopherol, d-alpha tocopheryl acetate, d-alpha tocopheryl succinate and mixed tocopherols, an analog of vitamin E or a combination thereof.

The vitamin C in the formulation may, for example, be in the form of ascorbic acid. In certain embodiments, a formulation of the present invention may include a derivative of vitamin C including but not limited to one or more salts of ascorbic acid, an analog of vitamin C or a combination thereof. Examples include, but are not limited to, calcium ascorbate, sodium ascorbate, and other mineral ascorbates; ascorbic acid with bioflavonoids; and combination products, such as Ester-C®, which contains calcium ascorbate, dehydroascorbate, calcium threonate, xylonate and lyxonate.

In certain embodiments, a formulation of the present invention may include vitamin K or a derivative of vitamin K including but not limited to menaquinone, an analog of vitamin K, isomer, or a combination thereof.

In certain embodiments, a formulation of the present invention may include calcium or a derivative of calcium including but not limited to calcium lactate or other calcium salt, an analog or a combination thereof. In certain embodiments of the invention, one or more various calcium salts may be used. Some representative salts of calcium include, for example, but not limited to, the acetate, lactobionate, carbonate, chloride, gluconate, and phosphate salts of calcium.

In certain embodiments, a formulation of the present invention may include iodine or a derivative of iodine including but not limited to iodide, a salt form, an analog or a combination thereof. Representative iodide salts that may be used include, but are not limited to, potassium iodide, sodium iodide, and calcium iodide.

In certain embodiments, a formulation of the present invention may include magnesium or a derivative of magnesium including but not limited to magnesium bis/glycinate, other magnesium salt, an analog or a combination thereof. Other representative magnesium salts that may be used include, but are not limited to, magnesium chloride and magnesium sulfate.

In certain embodiments, a formulation of the present invention may include zinc or a derivative of zinc including but not limited to zinc citrate (for instance, 40% elemental), other zinc salt, an analog or a combination thereof. Other representative zinc salts that may be used include, for example, zinc gluconate.

In certain embodiments, a formulation of the present invention may include selenium or a derivative of selenium including but not limited to AA complex and chelate (L-selenomethionine), an analog or a combination thereof.

In certain embodiments, a formulation of the present invention may include manganese or a derivative of manganese including but not limited to manganese bisglycinate/chelate, an analog, or a combination thereof.

In certain embodiments, a formulation of the present invention may include chromium or a derivative of chromium including but not limited to nicotinate glycinate chelate, an analog, or a combination thereof.

In certain embodiments, a formulation of the present invention may include molybdenum or a derivative of molybdenum including, for instance, glycinate/chelate, an analog, or a combination thereof.

In certain embodiments, a formulation of the present invention may include trimethyglycine (betaine) or a derivative of betaine, an analog of betaine or a combination thereof. Representative forms that may be used include, for example, betaine anhydrous, betaine hydrochloride, and glycine betaine.

In certain embodiments, a formulation of the present invention may include choline or a derivative of choline including but not limited to choline bitartrate, an analog or a combination thereof.

In certain embodiments, a formulation of the present invention may include carnitine or a derivative of carnitine including but not limited to the biologically active enantiomer L-carnitine, acetyl-L-carnitine, glycine propionyl-L-carnitine (GPLC), an analog or a combination thereof.

In certain embodiments, a formulation of the present invention may include N-acetyl cysteine or a derivative of N-acetyl cysteine, an analog of N-acetyl cysteine or a combination thereof.

In certain embodiments, a formulation of the present invention may include milk thistle (*Silybum marianum*) or a derivative of milk thistle, an analog of milk thistle or a combination thereof. It is understood that milk thistle (*Silybum marianum*) has other accepted and established names including, for example, *Cardus marianus*, milk thistle, blessed milk thistle, Marian thistle, Marythistle, Saint Mary's thistle, Mediterranean milk thistle, variegated thistle and Scotch thistle. The species of *Silybum marianum* that is preferred is obtained from a plant of the Asteraceae family.

The creatine in the formulation may be a derivative of creatine, an analog of creatine or a combination thereof. Representative forms of creatine include, for example, pure or substantially pure creatine magnesium chelate, creatine Monohydrate, and creatine pyruvate. Other suitable forms of creatine may also be used.

In another embodiment, the ingredients in the formulation may be in the pure, substantially pure or synthetic form. In yet another embodiment, a representative formulation comprises about 0.1 mg-10 mg, preferably about 0.5 mg of thiamin, about 0.1 mg-500 mg, preferably about 5 mg of riboflavin, about 0.5 mg-1 g, preferably about 5 mg of niacin, about 0.5 mg-10 mg, preferably about 2 mg of pantothenic acid, about 0.1 mg-25 mg, preferably about 2 mg of Vitamin B6, about 5 mcg-1 mg, preferably about 100 mcg of folate, about 1 mcg-5,000 mcg, preferably about 50 mcg of cobalamin, about 10 mcg-1,000 mcg, preferably about 100 mcg of Vitamin A, about 50 IU-1,000 IU, preferably about 400 IU of Vitamin D, about 1 mg-20 mg, preferably about 5 mg of Vitamin E, about 5 mg-5,000 mg, preferably about 50 mg of Vitamin C, about 0.5 mcg-300 mcg, preferably about 2.5 mcg of Vitamin K, about 50 mg-800 mg, preferably about 200 mg of calcium, about 20 mcg-15 mg, preferably about 130 mcg iodine, about 5 mg-200 mg, preferably about 75 mg of magnesium, about 1 mg-15 mg, preferably about 2.5 mg of zinc, about 5 mcg-200 mcg, preferably about 25 mcg of selenium, about 0.1 mg-5 mg, preferably about 0.6 mg of manganese, about 1 mcg-150 mcg, preferably about 10 mcg of chromium, about 1 mcg-100 mcg, preferably about 20 mcg of molybdenum, about 100 mg-5 g, preferably about 500 mg of trimethylglycine (betaine), about 10 mg-1 g, preferably about 20 mg of choline, about 50 mg-2 g, preferably about 200 mg of acetyl-L-carnitine, about 20 mg-500 mg, preferably about 100 mg of N-acetyl cysteine, about 50 mg-800 mg, preferably about 200 mg of milk thistle (*Silybum marianum,* 80% silymarin), and about 20 mg-800 mg, preferably about 100 mg of creatinine.

The formulations of the present invention preferably have further beneficial effects on various metabolic and biochemical reactions and systems including but not limited to the immune system, detoxification, cell membrane integrity, s-adenosylmethionine (SAM) production, DNA synthesis and repair, glutathione production and the nervous system.

Moreover, the formulations of the present invention preferably maintain balance, or substantially maintain balance between oxidative stress and methylation, maintains balance between Th 1 and Th2 responses or both.

In certain embodiments, the formulations of the present invention may be administered in a form including but not limited to capsules, tablets, syrups, liquids, and injectables. The formulations may be administered using any suitable dosage form. Moreover, the preparation of the formulations of the present invention is not limited to a specific manufacturing process.

It is to be understood that the formulations of the present invention can also be prepared and administered with any pharmaceutically acceptable carrier or carriers. Moreover, a formulation of the present invention can also be prepared in such a manner that the formulation comprises one or more pharmaceutically acceptable excipients. Examples of some of the various classes or types of excipients that may be used in preparation of the formulations include, but are not limited to, flavoring agents, coloring agents, stabilizing agents, binders, disintegrants, and other well-accepted types of excipients that are safe and effective for human use and consumption. Because it is well understood that the number and type of specific excipients is too exhaustive and numerous to be listed here, it is to be understood that the inventors of the present invention have contemplated that the formulations of the present invention may comprise any suitable combination of one or more pharmaceutically acceptable excipients, for instance, for preparation and manufacturing of the formulations. Such representative excipients that may be used for preparation of the formulations (for instance, for preparation of a suitable dosage form for administration of a formulation) may include, but are not limited to, one or more of the pharmaceutically acceptable excipients disclosed in the "*Handbook of Pharmaceutical Excipients*"

(sixth edition, edited by Rowe, Sheskey and Quinn), which is herein incorporated by reference.

In still yet another embodiment, the formulations of the present invention may be administered via routes including but not limited to oral, intramuscular, intradermal, intravenous, nasal, subcutaneous, or intraperitoneal. In further yet another embodiment, the formulation is administered prior to, concurrent with or subsequent to the vaccination.

In another embodiment, the present invention provides a method to support an individual's body during vaccination. In yet another embodiment, the individual is an infant, a toddler, a teenager or an adult.

The formulation described herein can be administered to an individual and any suitable and well-established biochemical assay(s) can be used for accurate and reliable testing, analysis and measurement of the disclosed and claimed biomarkers. The levels of these biomarkers can be measured at DNA, RNA and/or protein level using assays that are known in the art. According to one preferred embodiment, one or more human biomarkers can be evaluated in vitro or ex vivo before and after the administration of the formulation describe herein. For instance, samples including but not limited to blood, serum, or plasma may be collected by any method known in the art prior to and/or after the administration of the formulation described herein to an individual by any of the means described herein or known in the art. A suitable, reliable, and accurate assay or assays can be used for accurate and reliable analysis and measurement of one or more biomarkers described herein, for instance, cytokines released by Th1 and Th2 cells. In accordance with the present invention, one representative approach/methodology that can be used for the detection of biomarkers, e.g. from human serum is described in (*"Highly Sensitive Diagnostic Assay for the Detection of Protein Biomarkers Using Microresonators and Multifunctional Nanoparticles"*, ACS Nano, 2012, 6(5), pp 4375-4381.) Other representative analytical in vitro and/or ex vivo methods or procedures for the detection of the biomarkers described herein include but are not limited to intracellular cytokine staining, flow cytometry, Elispot assay, RNAse protection assay, Northern blot, and ELISA.

In another preferred embodiment, the method of analyzing the degree or percentage of methylation includes but is not limited to Polymerase Chain Reaction (PCR) or DNA sequencing.

The foregoing descriptions of the embodiments of the present invention have been presented for purposes of illustration and description. They are not intended to be exhaustive or to limit the present invention to the precise forms disclosed. The exemplary embodiments were chosen and described in order to best explain the principles of the present invention and its practical application, to thereby enable others skilled in the art to best utilize the present invention.

What is claimed is:

1. A method of supporting the healthy state of an individual's body in conjunction with receipt of vaccinations and during adaptive immune responses which target immune system homeostasis, comprising:
    administering a pharmacologically acceptable amount, to an individual, of the following formulation:
    1 mg-10 mg of thiamin (Vitamin B1), 0.1 mg-500 mg of riboflavin (Vitamin B2), 0.5 mg-1 g of niacin (Vitamin B3), 0.5 mg-10 mg of pantothenic acid (Vitamin B5), 0.1 mg-25 mg of pyridoxine (Vitamin B6), 5 mcg-1 mg of folate (vitamin B9), 10 mcg-5,000 mcg of cobalamin (Vitamin B12), 10 mcg-1,000 mcg of Vitamin A, 50 IU-1,000 IU of Vitamin D, 1 mg-20 mg of Vitamin E, 5 mg-5,000 mg of Vitamin C, 0.5 mcg-300 mcg, of Vitamin K, 50 mg-800 mg of Calcium, 20 mcg-15 mg of Iodine, 5 mg-200 mg of Magnesium, 1 mg-15 mg of Zinc, 5 mcg-200 mcg of Selenium, 0.1 mg-5 mg of Manganese, 1 mcg-150 mcg of chromium, 1 mcg-100 mcg of molybdenum, 10 mg-1 g of trimethylglycine (betaine), 10 mg-1 g of choline, 50 mg-2 g of acetyl-L-carnitine, 20 mg-500 mg of N-acetyl cysteine, 50 mg-800 mg, of milk thistle and 20 mg-800 mg of creatinine or a combination thereof;
    administering said formulation prior to the administration of a vaccine, concurrent with the administration of a vaccine or subsequent to the administration of a vaccine; and
    administrating said formulation to said individual where the individual is an infant, a toddler, a teenager or an adult.

2. The method of claim 1, wherein said administered formulation is administered orally, intramuscularly, intradermally, intravenously, nasally, subcutaneously, intraperitoneally or by any other suitable route of administration.

3. The method of claim 1, wherein said administered formulation is delivered via capsules, tablets, syrups, liquids, injectables or any suitable dosage forms.

4. The method of claim 1, wherein said administered formulation further comprises:
    a pharmaceutically acceptable carrier or carriers; and
    a pharmaceutically acceptable excipient or excipients including flavoring agents, coloring agents, stabilizing agents, binders, fillers, disintegrants, diluents and/or other well-accepted types of excipients that are safe and effective for human use and consumption.

\* \* \* \* \*